(12) United States Patent
Ghivizzani

(10) Patent No.: US 11,207,382 B2
(45) Date of Patent: Dec. 28, 2021

(54) COMPOSITIONS FOR TREATING CONDITIONS USING RECOMBINANT SELF-COMPLEMENTARY ADENO-ASSOCIATED VIRUS

(71) Applicant: University of Florida Research Foundation, Incorporated, Gainesville, FL (US)

(72) Inventor: Steven C. Ghivizzani, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/326,488

(22) PCT Filed: Aug. 18, 2017

(86) PCT No.: PCT/US2017/047589
§ 371 (c)(1),
(2) Date: Feb. 19, 2019

(87) PCT Pub. No.: WO2018/035451
PCT Pub. Date: Feb. 22, 2018

(65) Prior Publication Data
US 2019/0381140 A1 Dec. 19, 2019

Related U.S. Application Data

(60) Provisional application No. 62/377,297, filed on Aug. 19, 2016.

(51) Int. Cl.
| | | |
|---|---|---|
| *A61K 38/20* | (2006.01) | |
| *A61K 35/761* | (2015.01) | |
| *A61K 9/00* | (2006.01) | |
| *A61K 35/32* | (2015.01) | |
| *A61K 45/06* | (2006.01) | |

(52) U.S. Cl.
CPC ........ *A61K 38/2006* (2013.01); *A61K 9/0019* (2013.01); *A61K 35/32* (2013.01); *A61K 35/761* (2013.01); *A61K 45/06* (2013.01)

(58) Field of Classification Search
CPC .. A61K 38/2006; A61K 48/00; A61K 9/0019; A61K 35/761; A61K 45/06; A61K 35/32; C12N 2750/14143; C07K 14/545; A61P 19/02
See application file for complete search history.

(56) References Cited

U.S. PATENT DOCUMENTS

| | | |
|---|---|---|
| 5,747,072 A | 5/1998 | Davidson et al. |
| 5,756,283 A | 5/1998 | Wilson et al. |
| 6,040,183 A | 3/2000 | Ferrari et al. |
| 6,083,716 A | 7/2000 | Wilson et al. |
| 6,093,570 A | 7/2000 | Ferrari et al. |
| 6,429,001 B1 | 8/2002 | Hardy |
| 6,482,634 B1 | 11/2002 | Wilson et al. |
| 6,491,907 B1 | 12/2002 | Rabinowitz et al. |
| 6,548,286 B1 | 4/2003 | Samulski et al. |
| 6,943,153 B1 | 9/2005 | Manning et al. |
| 6,951,758 B2 | 10/2005 | Ferrari et al. |
| 7,037,492 B2 | 5/2006 | Glorioso et al. |
| 7,229,823 B2 | 6/2007 | Samulski et al. |
| 7,439,065 B2 | 10/2008 | Ferrari et al. |
| 7,452,696 B2 | 11/2008 | Chen et al. |
| 7,465,583 B2 | 12/2008 | Samulski et al. |
| 7,790,154 B2 | 9/2010 | Samulski et al. |
| 7,892,809 B2 | 2/2011 | Bowles et al. |
| 7,892,824 B2 | 2/2011 | Duan et al. |
| 8,361,457 B2 | 1/2013 | Samulski et al. |
| 8,529,885 B2 | 9/2013 | Tak et al. |
| 8,736,207 B2 | 5/2014 | Ritter et al. |
| 8,809,058 B2 | 8/2014 | Ferrari et al. |
| 8,999,948 B2 | 4/2015 | Tubert et al. |
| 2004/0237145 A1 | 11/2004 | Graham et al. |
| 2006/0014966 A1 | 1/2006 | Lee et al. |
| 2007/0009899 A1 | 1/2007 | Mounts |
| 2007/0042462 A1* | 2/2007 | Hildinger ............... C12N 15/86 435/69.1 |
| 2007/0128177 A1 | 6/2007 | Burstein et al. |
| 2008/0166762 A1 | 7/2008 | Shivraj et al. |

(Continued)

FOREIGN PATENT DOCUMENTS

| | | |
|---|---|---|
| CN | 103509100 A | 1/2014 |
| JP | 2002538770 A | 11/2002 |

(Continued)

OTHER PUBLICATIONS

Fath et al PLoS One 6e 17596 (Year: 2011).*
Husain et al Gene Therapy 16, 927-932 (Year: 2009).*
Goodrich et al Molecular Therapy—Nucleic Acids 2, e70;1-10 (Year: 2013).*
U.S. Appl. No. 16/467,141, filed Jun. 6, 2019, Ghivizzani.
PCT/US2017/047589, Feb. 28, 2019, International Preliminary Report on Patentability.
Extended European Search Report for Application No. EP 17842207.7 dated Mar. 3, 2020.
International Search Report and Written Opinion for Application No. PCT/US2017/065173 dated May 6, 2018.
International Preliminary Report on Patentability for Application No. PCT/US2017/065173 dated Jun. 11, 2019.

(Continued)

*Primary Examiner* — Anoop K Singh
(74) *Attorney, Agent, or Firm* — Wolf, Greenfield & Sacks, P.C.

(57) ABSTRACT

Methods and compositions for treating symptoms of conditions such as but not limited to osteoarthritis and rheumatoid arthritis. The methods may feature direct intraarticular injection of a recombinant self-complementary adeno-associated virus (sc-rAAV) with a vector adapted to express a modified IL-1Ra peptide. The methods of the present invention may express a therapeutically effective amount of the modified IL-1Ra peptide so as to ameliorating symptoms associated with the condition being treated.

7 Claims, 1 Drawing Sheet
Specification includes a Sequence Listing.

(56) References Cited

U.S. PATENT DOCUMENTS

| | | | |
|---|---|---|---|
| 2008/0187576 A1* | 8/2008 | Ghivizzani | A61K 31/7088 424/450 |
| 2009/0104155 A1 | 4/2009 | Goodrich et al. | |
| 2009/0105148 A1 | 4/2009 | Aikawa et al. | |
| 2011/0076285 A1 | 3/2011 | Stalmans et al. | |
| 2012/0232130 A1 | 9/2012 | Cepko et al. | |
| 2012/0237587 A1 | 9/2012 | Wehling et al. | |
| 2013/0217864 A1* | 8/2013 | Cho | C07K 14/54 530/387.3 |
| 2013/1021786 | 8/2013 | Cho et al. | |
| 2013/0295614 A1 | 11/2013 | Hareendran et al. | |
| 2014/0107189 A1 | 4/2014 | Bancel et al. | |
| 2014/0141067 A1* | 5/2014 | Bancel | C07K 14/4746 424/450 |
| 2014/0234255 A1 | 8/2014 | Lai et al. | |
| 2015/0031083 A1 | 1/2015 | Lee et al. | |
| 2015/0050238 A1 | 2/2015 | Kamath | |
| 2015/0218586 A1 | 8/2015 | Schleef | |
| 2015/0353938 A1 | 12/2015 | Ye et al. | |
| 2015/0361452 A1 | 12/2015 | Ruan et al. | |
| 2016/0068844 A1 | 3/2016 | Wadsworth et al. | |

FOREIGN PATENT DOCUMENTS

| | | | |
|---|---|---|---|
| JP | 2010516252 A | 5/2010 | |
| JP | 2015518816 A | 7/2015 | |
| KR | 2003028080 A | 11/2003 | |
| KR | 2002027450 A | 3/2005 | |
| KR | 2012041139 A | 4/2012 | |
| WO | WO1995016353 A1 | 6/1995 | |
| WO | WO2002038782 A2 | 5/2002 | |
| WO | WO 2002/062375 A1 | 8/2002 | |
| WO | WO2004092211 A1 | 10/2004 | |
| WO | WO2007039699 A3 | 5/2007 | |
| WO | WO2008088895 A2 | 7/2008 | |
| WO | WO 2008/132485 A2 | 11/2008 | |
| WO | WO2012047093 A1 | 4/2012 | |
| WO | WO2013151672 A2 | 10/2013 | |
| WO | WO2014170470 A1 | 10/2014 | |
| WO | WO2015018860 A1 | 2/2015 | |
| WO | WO2015031392 A1 | 3/2015 | |
| WO | WO2015044292 A1 | 4/2015 | |
| WO | WO2015158749 A3 | 10/2015 | |
| WO | WO2015168666 A2 | 11/2015 | |
| WO | WO-2015168666 A2 * | 11/2015 | A61P 25/14 |
| WO | WO2018035441 A1 | 2/2018 | |
| WO | WO2018035451 A1 | 2/2018 | |
| WO | WO2018035457 A1 | 2/2018 | |
| WO | WO 2018/106956 A2 | 6/2018 | |

OTHER PUBLICATIONS

Chang et al., The production and characterization of a modified recombinant interleukin-1 receptor antagonist. Immunol Invest. Jul. 1996;25(4):355-68.
Goodrich et al., scAAVIL-1ra dosing trial in a large animal model and validation of long-term expression with repeat administration for osteoarthritis therapy. Gene Ther. Jul. 2015;22(7):536-45. doi: 10.1038/gt.2015.21. Epub Apr. 23, 2015.
Kay et al., Intra-articular gene delivery and expression of interleukin-1Ra mediated by self-complementary adeno-associated virus. J Gene Med. Jul. 2009;11(7):605-14.
Kay et al., Self-Complementary Vectors Significantly Enhance AAV-Mediated Gene Transfer to Joint Tissues. Mol Ther. Jan. 1, 2006;13:S420-1.
Pan et al., Therapy and prevention of arthritis by recombinant adeno-associated virus vector with delivery of interleukin-1 receptor antagonist. Arthritis Rheum. Feb. 2000;43(2):289-97.
International Preliminary Report on Patentability for Application No. PCT/US2017/047589 dated Feb. 28, 2019.
International Search Report Issued For PCT Application No. PCT/US2017/047572 dated Nov. 13, 2017.
Goodrich et al. "Optimization of scAAVIL-1 ra In Vitro and In Vivo to Deliver High Levels of 1-67 Therapeutic Protein for Treatment of Osteoarthritis," Molecular Therapy-Nucleic Acids, Feb. 5, 2013 vol. 2, e70.
Evans et al. "Clinical Trial to Assess the Safety, Feasibility, and Efficacy of Transferring a Potentially Anti-Arthritic Cytokine Gene to Human Joints with Rheumatoid Arthritis", Human Gene Therapy, 1996, 7:1261-1280.
Evans et al. "Gene Transfer to Human Joints: Progress Towards a Gene Therapy of Arthritis", 2005, PNAS 102 (24):8698-8703.
Frisbie et al. "Treatment of Experimental Equine Osteoarthritis by In Vivo Delivery of the Equine lnterleukin-1 Receptor Antagonist Gene", Gene Therapy, 2002, 9(1): 12-20.
Wang et al. "Phase 1 Studies of Anti-Interleukin-1 Dual-Variable Domain Immunoglobulin in Healthy Subjects and Patients with Osteoarthritis", Osteoarthritis and Cartilage, 2015, 23:A398-399.
Wang et al. "Interleukin-1 Dual Variable Domain Immunoglobulin, a new Potential Treatment for Osteoarthritis", Osteoarthritis and cartilage, 2014, 22:S462-S463.
Wang et al., "Interleukin-1 Dual Variable-Domain Immunoglobulin Reduces Multiple Imflammatory Markers in Knee Osteoarthritis patients" Scientific Abstracts, 2014, SAT0448.
Wang et al. "lnterleukin-1 Dual-Variable Domain Immunoglobulin Reduces Multiple Inflammatory Markers in Knee Osteoarthritis Patients", 2014 ACR/ARHP Annual Meeting Abstract No. 2237.
Wang et al. "Dual Variable Domain-lmmunoglobulin (Dvd-Iga"q Abt-981 Simultaneously and Dose-Dependently Inhibits lnterleukin-1 i'lpha and -1 i'eta in Subjects with Knee Osteoarthritis", 2015 ACR/ARHP Annual Meeting Abstract No. 318.
Kamath et al. "Simultaneous Targeting of IL-1a and IL-1b by a Dual-Variabledomain Immunoglobulin (dvd-ig™) Prevents Cartilage Degradation in Preclinical Models of Osteoarthritis" Osteoarthritis and Cartilage, 2011, 19S1:S64.
Lacy et al. "Generation and Characterization of ABT-981, a Dual Variable Domain Immunoglobulin (DVD-IgTM) Molecule that Specifically and Potently Neutralizes Both IL-1α and IL-1β", mAbs, 2015, 7(3):605-619.
Goss et al. "Safety, Tolerability and Pharmacokinetics of ABT-981, an IL-1A and IL-1β Dual Target Biologic Drug in Development for Osteoarthritis, Following Single Dose Administration in Healthy Subjects", Scientific Abstracts, 2014, SAT0447 p. 755-756.
Wu et al. "Molecular construction and optimization of anti-human IL-1α/β dual variable domain immunoglobulin (DVD-IgTM) molecules", mAbs, 2009, 1(4):339-347.
Smith & Waterman "Comparison of Biosequences", Adv. Appl. Math. 1981, 2:482.
Needleman & Wunsch, "A General Method Applicable to the Search for Similarities in the Amino Acid Sequence of Two Proteins" J. Mol. Biol. 1970, 48:443.
Pearson & Lipman "Improved tools for biological sequence comparison", Proc. Natl. Acad. Sci. USA, 1988, 85:2444.
Higgins & Sharp "Clustal: a package for performing multiple sequence alignment on a microcomputer", Gene, 1988, 73:237-44.
Higgins & Sharp "Fast and sensitive multiple sequence alignments on a microcomputer", CABIOS, 1989, 5:151-3.
Corpet et al. "Multiple sequence alignment with hierarchical clustering", Nuc. Acids Res. 1988, 16:10881-90.
Huang et al. "Parallelization of a local similarity algorithm" Computer Appls. In the Biosciences, 1992, 8, 155-65.
Altschul et al. "Basic Local Alignment Search Tool", J. Mol. Biol. 1990, 215:403-10.
Kent "BLAT—The BLAST-Like Alignment Tool", Genome Res. 2002, 12:656-664.
Van De Loo et al. "An inflammation-inducible adenoviral expression system for local treatment of the arthritic joint" Gene Therapy, 2004, 11:581-590.
International Search Report Issue for PCT Application No. PCT/US2017/047589 dated Aug. 11, 2017.
International Search Report Issue for PCT Application No. PCT/US2017/047607 dated Aug. 11, 2017.
Wang et al. "Safety and biodistribution assessment of sc-rAAV2.5IL-1Ra administered via intra-articular injection in a mono-

(56) References Cited

OTHER PUBLICATIONS iodoacetate-induced osteoarthritis rat model," Molecular Therapy—Methods & Clinical Development, Jan. 13, 2016. vol. 3.

"AY026462.1: Canis familiaris interleukin-1 receptor antagonist mRNA, complete cds," 68.71.72.74 GenBank. Feb. 12, 2001 (Feb. 12, 2001), pp. 1-12. Retrieved from the Internet: <https:flwww.ncbi.nlm.nih.gov/nuccore/AY026462.1>on Oct. 14, 2017.

Cao et al. "Therapeutic targeting and rapid mobilization of endosteal HSC using a small molecule integrin antagonist" Nature Communications, 2016, 7:11007.

Pepinsky et al. "Comparative Assessment of the Ligand and Metal Ion Binding Properties of Integrins R9â1 and R4â1" Biochemistry, 2002, 41, 7125-7141.

Watson et al. "ScAAV-Mediated Gene Transfer of Interleukin 1-Receptor Antagonist to Synovium and Articular Cartilage in Large Mammalian Joints" Gene Ther, 2013, 20(6): 670-677.

PCT/US2017/065173, May 9, 2018, International Search Report and Written Opinion.

PCT/US2017/065173, Jun. 11, 2019, International Preliminary Report on Patentability.

EP 17842207.7, Mar. 3, 2020, Extended European Search Report.

Extended European Search Report for Application No. EP 17878272.8 dated Jun. 9, 2020.

Garmory et al., DNA vaccines: improving expression of antigens. Genet Vaccines Ther. Sep. 16, 2003;1(1):2. doi: 10.1186/1479-0556-1-2.

EP 17878272.8, Jun. 9, 2020, Extended European Search Report.

\* cited by examiner

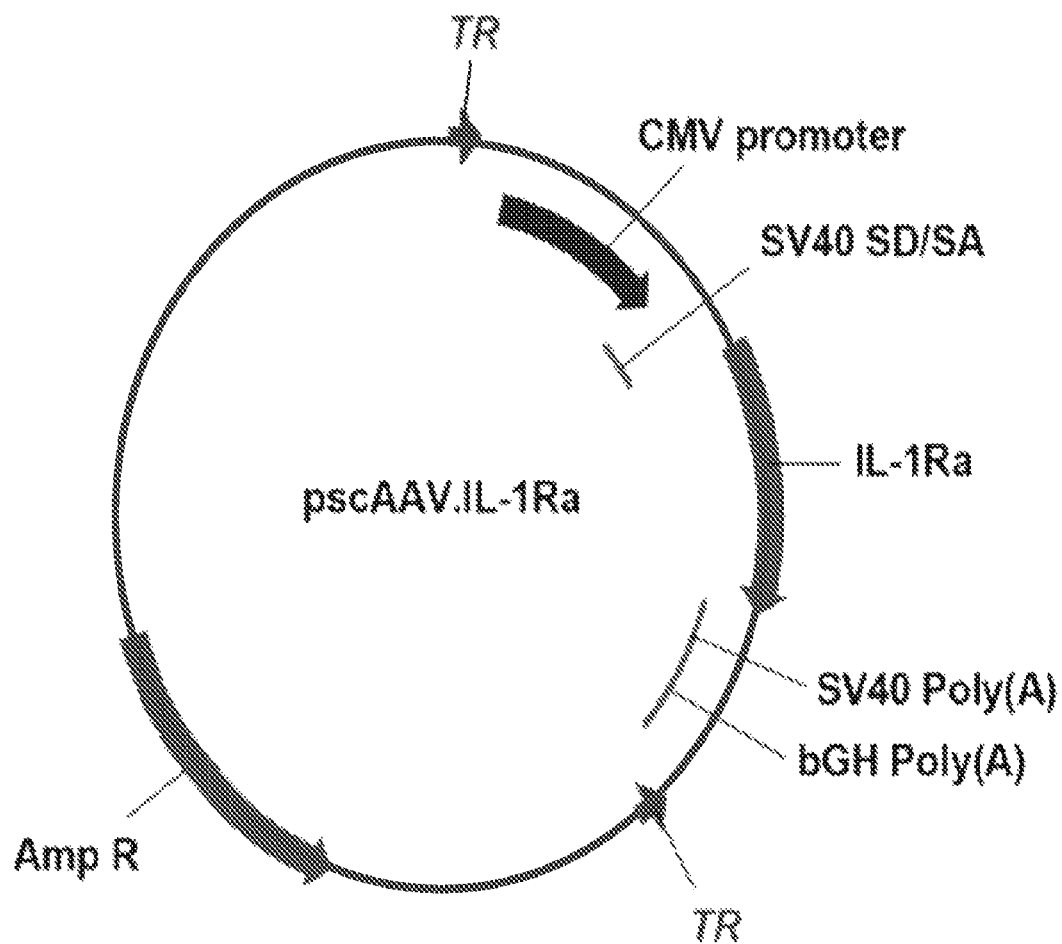

SEQUENCE LISTING

<160> NUMBER OF SEQ ID NOS: 7

<210> SEQ ID NO 1
<211> LENGTH: 5718
<212> TYPE: DNA

-continued

<213> ORGANISM: Artificial Sequence
<220> FEATURE:
<223> OTHER INFORMATION: Sequence of Hu-IL-1Ra plasmid containing entire viral sequence with modified human IL1Ra insert and the SacII / NotI restriction sites.

<400> SEQUENCE: 1

```
cattaatgaa tcggccaacg cgcggggaga ggcggtttgc gtattgggcg ctcttccgct     60
tcctcgctca ctgactcgct gcgctcggtc gttcggctgc ggcgagcggt atcagctcac    120
tcaaaggcgg taatacggtt atccacagaa tcaggggata acgcaggaaa gaacatgtga    180
gcaaaaggcc agcaaaaggc caggaaccgt aaaaaggccg cgttgctggc gtttttccat    240
aggctccgcc cccctgacga gcatcacaaa aatcgacgct caagtcagag gtggcgaaac    300
ccgacaggac tataaagata ccaggcgttt ccccctggaa gctccctcgt gcgctctcct    360
gttccgaccc tgccgcttac cggatacctg tccgcctttc tcccttcggg aagcgtggcg    420
ctttctcata gctcacgctg taggtatctc agttcggtgt aggtcgttcg ctccaagctg    480
ggctgtgtgc acgaaccccc cgttcagccc gaccgctgcg ccttatccgg taactatcgt    540
cttgagtcca acccggtaag acacgactta tcgccactgg cagcagccac tggtaacagg    600
attagcagag cgaggtatgt aggcggtgct acagagttct tgaagtggtg gcctaactac    660
ggctacacta gaaggacagt atttggtatc tgcgctctgc tgaagccagt taccttcgga    720
aaaagagttg gtagctcttg atccggcaaa caaaccaccg ctggtagcgg tggttttttt    780
gtttgcaagc agcagattac gcgcagaaaa aaaggatctc aagaagatcc tttgatcttt    840
tctacggggt ctgacgctca gtggaacgaa aactcacgtt aagggatttt ggtcatgaga    900
ttatcaaaaa ggatcttcac ctagatcctt ttaaattaaa aatgaagttt taaatcaatc    960
taaagtatat atgagtaaac ttggtctgac agttaccaat gcttaatcag tgaggcacct   1020
atctcagcga tctgtctatt tcgttcatcc atagttgcct gactccccgt cgtgtagata   1080
actacgatac gggagggctt accatctggc cccagtgctg caatgatacc gcgagaccca   1140
cgctcaccgg ctccagattt atcagcaata aaccagccag ccggaagggc cgagcgcaga   1200
agtggtcctg caactttatc cgcctccatc cagtctatta attgttgccg ggaagctaga   1260
gtaagtagtt cgccagttaa tagtttgcgc aacgttgttg ccattgctac aggcatcgtg   1320
gtgtcacgct cgtcgtttgg tatggcttca ttcagctccg gttcccaacg atcaaggcga   1380
gttacatgat cccccatgtt gtgcaaaaaa gcggttagct ccttcggtcc tccgatcgtt   1440
gtcagaagta agttggccgc agtgttatca ctcatggtta tggcagcact gcataattct   1500
cttactgtca tgccatccgt aagatgcttt tctgtgactg gtgagtactc aaccaagtca   1560
ttctgagaat agtgtatgcg gcgaccgagt tgctcttgcc cggcgtcaat acgggataat   1620
accgcgccac atagcagaac tttaaaagtg ctcatcattg gaaaacgttc ttcggggcga   1680
aaactctcaa ggatcttacc gctgttgaga tccagttcga tgtaacccac tcgtgcaccc   1740
aactgatctt cagcatcttt tactttcacc agcgtttctg ggtgagcaaa aacaggaagg   1800
caaaatgccg caaaaaaggg aataagggcg acacggaaat gttgaatact catactcttc   1860
ctttttcaat attattgaag catttatcag ggttattgtc tcatgagcgg atacatattt   1920
gaatgtattt agaaaaataa acaaataggg gttccgcgca catttccccg aaaagtgcca   1980
cctgacgtct aagaaaccat tattatcatg acattaacct ataaaaatag gcgtatcacg   2040
aggccctttc gtctcgcgcg tttcggtgat gacggtgaaa acctctgaca catgcagctc   2100
ccggagacgg tcacagcttg tctgtaagcg gatgccggga gcagacaagc ccgtcagggc   2160
```

```
gcgtcagcgg gtgttggcgg gtgtcgggc tggcttaact atgcggcatc agagcagatt    2220
gtactgagag tgcaccatat gcggtgtgaa ataccgcaca gatgcgtaag gagaaaatac    2280
cgcatcagga attccaacat ccaataaatc atacaggcaa ggcaaagaat tagcaaaatt    2340
aagcaataaa gcctcagagc ataaagctaa atcggttgta ccaaaaacat tatgaccctg    2400
taatactttt gcgggagaag cctttatttc aacgcaagga taaaatttt tagaaccctc    2460 atatatttta aatgcaatgc ctgagtaatg tgtaggtaaa gattcaaacg ggtgagaaag    2520
gccggagaca gtcaaatcac catcaatatg atattcaacc gttctagctg ataaattcat    2580
gccggagagg gtagctattt ttgagaggtc tctacaaagg ctatcaggtc attgcctgag    2640
agtctggagc aaacaagaga atcgatgaac ggtaatcgta aaactagcat gtcaatcata    2700
tgtaccccgg ttgataatca gaaaagcccc aaaaacagga agattgtata agcaaatatt    2760
taaattgtaa acgttaatat tttgttaaaa ttcgcgttaa attttgtta aatcagctca    2820 ttttttaacc aataggccga atcggcaaa atcccttata atcaaaaga atagaccgag    2880 atagggttga gtgttgttcc agtttggaac aagagtccac tattaaagaa cgtggactcc    2940
aacgtcaaag ggcgaaaaac cgtctatcag ggcgatggcc cactacgtga accatcaccc    3000
taatcaagtt ttttggggtc gaggtgccgt aaagcactaa atcggaaccc taaagggagc    3060
ccccgattta gagcttgacg gggaaagccg gcgaacgtgg cgagaaagga agggaagaaa    3120 gcgaaggag cgggcgctag ggcgctggca agtgtagcgg tcacgctgcg cgtaaccacc    3180
acacccgccg cgcttaatgc gccgctacag ggcgcgtact atggttgctt tgacgagcac    3240
gtataacgtg cttttcctcgt tagaatcaga gcgggagcta acaggaggc cgattaaagg    3300 gattttagac aggaacggta cgccagaatc ctgagaagtg ttttttataat cagtgaggcc    3360 accgagtaaa agagtctgtc catcacgcaa attaaccgtt gtcgcaatac ttctttgatt    3420
agtaataaca tcacttgcct gagtagaaga actcaaacta tcggccttgc tggtaatatc    3480
cagaacaata ttaccgccag ccattgcaac aggaaaaacg ctcatggaaa tacctacatt    3540
ttgacgctca atcgtctgga attccattcg ccattcaggc tgcgcaactg ttgggaaggg    3600
cgatcggtgc gggcctcttc gctattacgc cagctggcgc gctcgctcgc tcactgaggc    3660
cgcccgggca aagcccgggc gtcgggcgac cttggtcgc ccggcctcag tgagcgagcg    3720
agcgcgcaga gagggagtgg ccaactccat cactaggggt tccttgtagt taatgattaa    3780
cccgccatgc tacttatcta cgtagccatg ctcgatctga attcggtacc cgttacataa    3840
cttacggtaa atggcccgcc tggctgaccg cccaacgacc cccgcccatt gacgtcaata    3900
atgacgtatg ttcccatagt aacgccaata gggactttcc attgacgtca atgggtggag    3960
tatttacggt aaactgccca cttggcagta catcaagtgt atcatatgcc aagtacgccc    4020
cctattgacg tcaatgacgg taaatggccc gcctggcatt atgcccagta catgacctta    4080
tgggactttc ctacttggca gtacatctac gtattagtca tcgctattac catggtgatg    4140
cggttttggc agtacatcaa tgggcgtgga tagcggtttg actcacgggg atttccaagt    4200
ctccacccca ttgacgtcaa tgggagtttg ttttggcacc aaaatcaacg ggactttcca    4260
aaatgtcgta caactccgc cccattgacg caaatgggcg gtaggcgtgt acggtgggag    4320
gtctatataa gcagagctcg tttagtgaac cgtcagatcg cctggagacg ccatccacgc    4380
tgttttgacc tccatagaag acaccggac cgatccagcc tccggactct agaggatccg    4440
gtactcgagg aactgaaaaa ccagaaagtt aactggtaag tttagtcttt ttgtcttta    4500
```

```
tttcaggtcc cggatccggt ggtggtgcaa atcaaagaac tgctcctcag tggatgttgc    4560
ctttacttct aggcctgtac ggaagtgtta cttctgctct aaaagctgcg gaattgtacc    4620
cgcgggccac catggaaatc tgcagaggcc tgcggagcca cctgattacc ctgctgctgt    4680
tcctgttcca cagcgagaca atctgccggc ccagcggccg gaagtccagc aagatgcagg    4740
ccttccggat ctgggacgtg aaccagaaaa ccttctacct gcggaacaac cagctggtgg    4800
ccggataccT gcagggcccc aacgtgaacc tggaagagaa gatcgacgtg gtgcccatcg    4860
agccccacgc cctgtttctg ggcatccacg gcggcaagat gtgcctgagc tgcgtgaagt    4920
ccggcgacga gacaagactg cagctggaag ccgtgaacat caccgacctg agcgagaacc    4980
ggaagcagga caagagattc gccttcatca aagcgacag cggccccacc accagctttg    5040
agagcgccgc ctgccccggc tggttcctgt gtacagccat ggaagccgac cagcccgtgt    5100
ccctgacaaa catgcccgac gagggcgtga tggtcaccaa gttctatttt caagaagatg    5160
agtaataagc ggccgccggg atccagacat gataagatac attgatgagt ttggacaaac    5220
cacaactaga atgcagtgaa aaaatgctt tatttgtgaa atttgtgatg ctattgcttt    5280
atttgtaacc attataagct gcaataaaca agttaacaac aacaattgca ttcattttat    5340
gtttcaggtt caggggagg tgtgggaggt tttttagtcg actagagctc gctgatcagc    5400
ctcgactgtg ccttctagtt gccagccatc tgttgtttgc ccctccccg tgccttcctt    5460 gaccctggaa ggtgccactc ccactgtcct ttcctaataa aatgaggaaa ttgcatcgca    5520
ttgtctgagt aggtgtcatt ctattctggg ggtgggtg gggcaggaca gcaaggggga    5580
ggattgggaa gacaatagca ggaacccac tccctctctg cgcgctcgct cgctcactga    5640
ggccgggcga ccaaaggtcg cccgacgccc gggctttgcc cgggcggcct cagtgagcga    5700
gcgagcgcgc agctgctg                                                 5718

<210> SEQ ID NO 2
<211> LENGTH: 537
<212> TYPE: DNA
<213> ORGANISM: Artificial Sequence
<220> FEATURE:
<223> OTHER INFORMATION: Modified human IL-1Ra insert

<400> SEQUENCE: 2
atggaaatct gcagaggcct gcggagccac ctgattaccc tgctgctgtt cctgttccac      60
agcgagacaa tctgccggcc cagcggccgg aagtccagca gatgcaggc cttccggatc     120 tgggacgtga accagaaaac cttctacctg cggaacaacc agctggtggc cggatacctg     180
cagggcccca cgtgaacct ggaagagaag atcgacgtgg tgcccatcga gccccacgcc     240
ctgtttctgg gcatccacgg cggcaagatg tgcctgagct gcgtgaagtc cggcgacgag     300
acaagactgc agctggaagc cgtgaacatc accgacctga gcgagaaccg gaagcaggac     360
aagagattcg ccttcatcag aagcgacagc ggccccacca ccagctttga gagcgccgcc     420
tgccccggct ggttcctgtg tacagccatg gaagccgacc agcccgtgtc cctgacaaac     480
atgcccgacg agggcgtgat ggtcaccaag ttctatttc aagaagatga gtaataa         537

<210> SEQ ID NO 3
<211> LENGTH: 537
<212> TYPE: DNA
<213> ORGANISM: Artificial Sequence
<220> FEATURE:
<223> OTHER INFORMATION: Modified human IL-1Ra insert  (98% identical to
      SEQ ID NO: 2;
```

<400> SEQUENCE: 3

```
atggaaatct gcagaggact gcggagccac ctaattaccc tactccttt   cctgttccac     60
agcgagacaa tctgccggcc cagcggccgg aagtccagca agatgcaggc tttccggatc    120
tgggacgtga accagaaaac cttctacctc cggaacaacc agctggtggc gggatacctc    180
cagggcccca acgtgaacct agaagagaag atcgacgtgg tgcccatcga gccccacgcc    240
ctgtttctgg gcatccacgg cggcaagatg tgcctgagct gcgtgaagtc cggcgacgag    300
acaagactgc agctggaagc cgtgaacatc accgacctga gcgagaaccg gaagcaggac    360
aagagattcg ccttcatcag aagcgacagc ggccccacca ccagctttga gagcgccgcc    420
tgccccggct ggttcctgtg tacagccatg gaagccgacc agcccgtgtc cctgacaaac    480
atgcccgacg agggcgtgat ggtcaccaag ttctattttc aagaagatga gtaataa      537
```

<210> SEQ ID NO 4
<211> LENGTH: 537
<212> TYPE: DNA
<213> ORGANISM: Artificial Sequence
<220> FEATURE:
<223> OTHER INFORMATION: Modified human IL-1Ra insert (99% identical to SEQ ID NO: 2;

<400> SEQUENCE: 4

```
atggagatct gcagaggcct gcggagccat ctgattaccc tactgctttt cctgttccat     60
agcgagacaa tctgccggcc cagcggccgg aagtccagca aaatgcaggc cttccggatc    120
tgggacgtga accagaaaac cttctacctg cggaacaacc agctggtggc cggatacctg    180
cagggcccca acgtgaacct ggaagagaag atcgacgtgg tgcccatcga gccccacgcc    240
ctgtttctgg gcatccacgg cggcaagatg tgcctgagct gcgtgaagtc cggcgacgag    300
acaagactgc agctggaagc cgtgaacatc accgacctga gcgagaaccg gaagcaggac    360
aagagattcg ccttcatcag aagcgacagc ggccccacca ccagctttga gagcgccgcc    420
tgccccggct ggttcctgtg tacagccatg gaagccgacc agcccgtgtc cctgacaaac    480
atgcccgacg agggcgtgat ggtcaccaag ttctattttc aagaagatga gtaataa      537
```

<210> SEQ ID NO 5
<211> LENGTH: 537
<212> TYPE: DNA
<213> ORGANISM: Artificial Sequence
<220> FEATURE:
<223> OTHER INFORMATION: Modified human IL-1Ra insert (95% identical to SEQ ID NO: 2;

<400> SEQUENCE: 5

```
atggagatct gcagaggact gcggagccac ctaattaccc tactccttt   cctgttccat     60
agcgagacaa tctgccggcc cagcggccgg aagtccagca aaatgcaggc tttccggatc    120
tgggatgtga accagaagac cttctacctc cggaacaacc agctggtggc gggatacctc    180
cagggcccca acgtgaacct agaagagaag atcgacgtgg tgcccatcga gccccacgcc    240
ctgtttctgg gcatccatgg cggcaagatg tgtctgagtt gcgtgaagtc aggcgacgag    300
acaagactgc agctggaagc cgtgaacatc accgacctga gcgaaaaccg gaagcaggac    360
aagagattcg ccttcatcag aagcgacagc ggccccacca ctagctttga gagcgcagcc    420
tgccccggct ggttcctgtg tacagccatg gaggccgacc agcccgtgtc cctgacaaac    480
atgcctgacg aaggcgtgat ggtcaccaag ttctactttc aagaagatga ataataa      537
```

<210> SEQ ID NO 6
<211> LENGTH: 177
<212> TYPE: PRT
<213> ORGANISM: Homo sapiens

<400> SEQUENCE: 6

Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu

<210> SEQ ID NO 7
<211> LENGTH: 1165
<212> TYPE: DNA
<213> ORGANISM: Artificial Sequence
<220> FEATURE:
<223> OTHER INFORMATION: IL-1 beta/
     IL-6 hybrid promoter

<400> SEQUENCE: 7
atccaagagg gagaagaagc ccattggaga tgatgccata aaggaagtgg aagcgatatg      60
ataaaaatca tagtgcccat tcccaaataa tcccagaagc agaagggaaa ggagagaaat     120
atccacaaag acaggtgtgg gtacacacaa cattttcat actttaagat cccagaggac      180
tcatggaaat gatacaagaa aatgactcat aagaacaaat attaggaagc cagtgccaag     240
aatgagatgg gaaattgggg aaaatgttgg gggcagattg cttagttctg ttctaagcaa     300
gagggtgaac aaggaaggaa cagctcacta caaagaacag acatcactgc atgtacacac     360
aataatataa gaactaaccc atgattattt tgcttgtctt cttgttcaaa atgattgaag     420
accaatgaga tgagatcaac cttgataact ggctggcttc ggcatgatta gacacaagat     480
ggtatcaggg cacttgctgc tttgaataat gtcagtctcc tgtcttggaa gaatgacctg     540
acagggtaaa gaggaacttg cagctgagaa aggctttagt gactcaagag ctgaataatt     600
ccccaaaagc tggagcatcc tggcatttcc agctccccat ctctgcttgt tccacttcct     660
tggggctaca tcaccatcta catcatcatc actcttccac tccctccctt agtgccaact     720
atgtttatag cgagatattt tctgctcatt ggggatcgga aggaagtgct gtggcctgag     780

-continued

```
cggtctcctt gggaagacag gatctgatac atacgttgca caacctattt gacataagag    840
gtttcacttc ctgagatgga tgggatggta gcagatttgg gtccaggtta cagggccagg    900
atgagacatg gcagaactgt ggagactgtt acgtcagggg gcattgcccc atggctccaa    960
aatttccctc gagcctctgg ccccaccctc accctccaac aaagatttat caaatgtggg   1020
attttcccat gagtctcaat attagagtct caacccccaa taaatatagg actggagatg   1080
tctgaggctc attctgccct cgagcccacc gggaacgaaa gagaagctct atctcccctc   1140
caggagccca gctatgaact ccttc                                          1165
```

COMPOSITIONS FOR TREATING CONDITIONS USING RECOMBINANT SELF-COMPLEMENTARY ADENO-ASSOCIATED VIRUS

CROSS REFERENCE

This application is a national stage filing under 35 U.S.C. 371 of International Patent Application Serial No. PCT/US2017/047589, filed Aug. 18, 2017, which claims priority to U.S. Provisional Patent Application No. 62/377,297, filed Aug. 19, 2016, the specification(s) of each of which are incorporated herein in their entirety by reference.

REFERENCE TO SEQUENCE LISTING

Applicant asserts that the information recorded in the form of an Annex C/ST.25 text file submitted under Rule 13ter.1(a), entitled CALIM_16_02_PCT_Sequence_Listing_ST25.txt, is identical to that forming part of the international application as filed. The content of the sequence listing is incorporated herein by reference in its entirety.

FIELD OF THE INVENTION

The present invention relates to gene therapy and compositions for gene therapy, more particularly to recombinant self-complementary adeno-associated virus (sc-rAAV) and methods of treating conditions or symptoms of conditions using sc-rAAV.

BACKGROUND OF THE INVENTION

Osteoarthritis (OA) affects over 27 million Americans and is the leading cause of disability among the elderly. Patients with OA are also at higher risk of death. The cost of OA to our health care system is estimated to be over $100 billion per annum. Such statistics reflect the fact that OA is both incurable and remarkably resistant to treatment.

The earliest and predominant symptom of OA is pain. This normally arises late in the disease process, by which time there is often considerable structural alteration in the affected joint, including loss of articular cartilage, sclerosis of the sub-chondral bone, the formation of osteophytes, and synovial inflammation. In knee joints, there is also meniscal damage. In the absence of disease-modifying osteoarthritis drugs (DMOADs) that halt or reverse disease progression, present treatments are palliative. Because there currently is no effective way to intervene in the disease process, many patients progress to the point of needing total joint replacement surgery. While a successful procedure, this involves major, expensive surgery with extensive rehabilitation. In many cases, there is a need for revision surgery to replace a prosthetic joint that has become dysfunctional.

In the absence of DMOADs, the present standard of care is palliative. As reflected in the most recent guidelines for treating OA of the knee (the target joint of this IND) issued by the American College of Rheumatology (ACR) in 2012 and the American Academy of Orthopedic Surgeons (AAOS) in 2013, present approaches to treatment fall into three progressive categories. Non-pharmacological therapy includes a range of strategies such as patient education and self-help, exercise programs and weight loss. Pharmacological therapy includes the use of acetaminophen, non-steroidal anti-inflammatory drugs (NSAIDs), opiates and the intra-articular injection of glucocorticoids or hyaluronic acid. NSAIDs bring partial relief to many patients, but are associated with upper GI bleeding and kidney failure, of especial concern in the present context as many individuals with OA are elderly. The intraarticular injection of glucocorticoids brings rapid relief in many cases, but the effects usually persist for only a few weeks. Repeated injection of glucocorticoids is impractical and counter-indicated because of concerns about infection and evidence that sustained, high doses of glucocorticoids damage articular cartilage. The benefits of the intraarticular injection of hyaluronic acid (viscosupplementation) are disputed; the ACR makes no recommendation on this score, while the AAOS no longer recommends it. The intra-articular injection of mesenchymal stem cells (MSCs) and autologous blood products, such as platelet-rich plasma, is increasingly popular but not approved by the FDA for OA. The latest recommendations from the Osteoarthritis Research Society International and European League Against Rheumatism for treatment of OA of the knee do not differ greatly from those of the ACR and AAOS. The recommendations of the various bodies highlight the paucity of treatment options for OA and the complete lack of reliably effective pharmacologic interventions. Even when there is some response to therapy, it addresses only the signs and symptoms, not disease progression. When treatment fails to control the symptoms and progression of OA, surgical intervention may be indicated.

Arthroscopic lavage and debridement has been widely used to provide symptomatic relief, but its use has declined following evidence that its effects are no greater than placebo. An osteotomy is sometimes performed to realign the forces in the knee joint, so that load is now born by areas of intact cartilage. This measure can provide relief for several years until the newly weight-bearing articular cartilage erodes and symptoms reappear. In general, osteotomy is viewed as a delaying tactic that buys time until the surgical implantation of a prosthetic knee joint. Many patients progress to the point of needing total joint replacement, and over 700,000 artificial knees were surgically implanted last in year in the US.

IL-1 is a powerful mediator of both chondrocytic chondrolysis and suppression of matrix synthesis by chondrocytes. Together, these two processes are highly destructive to cartilage. IL-1 has also been shown to inhibit chondrogenesis but at the same time promote certain aspects of the osteogenic differentiation that could help account for the formation of osteophytes and sclerosis of sub-chondral bone. Paradoxically, IL-1 also promotes osteoclastic activity. By stimulating both osteogenesis and osteolysis, IL-1 would enhance bone turnover, as seen in the sub-chondral bone during OA. Finally, IL-1 is well positioned to provoke the inflammatory changes seen in OA. Its pyrogenic activities are known and the expression of vanishingly small amounts of IL-1 in the knee joints of rabbits is sufficient to elicit a pronounced synovitis.

In studying cartilage recovered from human joints with OA, the production of IL-1 by chondrocytes was found to be highly elevated and sustained in an autocrine fashion. Moreover, the cells did not produce IL-1Ra. This suggests enhanced autocrine and paracrine activation of chondrocytes by IL-1 in the absence of its major physiological inhibitor during OA. Enhanced responsiveness of chondrocytes to IL-1 in OA was also indicated by increased expression of the type I IL-1 receptor, the signaling receptor, on OA chondrocytes. The local production and consumption of IL-1 by chondrocytes may help explain why concentrations of IL-1 in synovial fluid tend to be low, even in OA. Also, genetic analyses have identified single nucleotide polymorphisms (SNPs) in the human gene encoding IL-1Ra (IL1RN) and regulatory elements that correlate with the incidence and severity of certain types of OA.

Targeted drug delivery is a major problem for the intra-articular treatment of joint diseases. Molecules of all sizes, as well as particles, are rapidly removed from joints via the lymphatics, subsynovial capillaries, or both. This makes it difficult to achieve sustained, therapeutic doses of anti-OA drugs in joints. To address this, small molecules can be delivered systemically, but proteins are difficult to deliver in this fashion because of size-dependent constraints in crossing the fenestrated endothelium of the synovial capillaries. Moreover, systemic delivery exposes non-target sites to high doses of the therapeutic, leading to unwanted side-effects. The rapid egress of proteins from joints, with half-lives typically of a few hours, makes intra-articular delivery potentially ineffective. As an example, recombinant IL-1Ra (Kineret, Amgen Biologicals) is delivered by daily subcutaneous injection in effort to treat symptoms of RA. However, daily delivery fails to maintain therapeutic serum levels of IL-1Ra between injections (Evans et al., 1996, Human Gene Therapy, 7:1261-1290; Evans et al., 2005, PNAS 102 (24): 8698-8703). Some studies have used ex vivo gene transfer for introducing IL-1Ra to treat OA. However, these approaches are laborious and have not seemed to provide long-term gene expression (Frisbie et al., 2002, Gene Therapy 9(1): 12-20). Also, several studies describe the use of a dual variable domain-immunoglobulin (DVD-Ig) targeting IL-1alpha and IL-1beta (e.g., ABT-981) for treating osteoarthritis (Kamath et al., 2011, Osteoarthritis and Cartilage 19S1:S64; Wang et al., 2015, Osteoarthritis and Cartilage 23:A398-399; Wang et al., 2014, Osteoarthritis and cartilage 22:S462-S463; Lacy et al., 2015, mAbs 7(3):605-619; Wu et al., 2009, mAbs 1(4):339-347; Wang et al., 2014, Scientific Abstracts SAT0448 pg. 756; Goss et al., 2014, Scientific Abstracts SAT0447 pg. 755-756; US 2015/0050238; Wang et al., 2014 ACR/ARHP Annual Meeting Abstract Number 2237; Wang et al., 2015 ACR/ARHP Annual Meeting Abstract Number 318). However, these peptides require repeated systemic introduction (e.g., 4 doses every 2 weeks or 3 doses every 4 weeks, e.g., by subcutaneous injection or intravenous infusion) because of the relatively short half-life (Wang et al., 2015, Osteoarthritis and Cartilage 23:A398-399; Wang et al., 2014, Osteoarthritis and cartilage 22:S462-S463; Evans et al., 2005, PNAS 102 (24): 8698-8703).

The present invention features methods and compositions for delivering a therapeutic gene product (e.g., IL-1Ra) in a sustained manner to a location of interest, e.g., joints. The present invention also features methods and compositions for treating symptoms of conditions such as but not limited to osteoarthritis and rheumatoid arthritis. The present invention also features methods and compositions for providing an individual (e.g., a human) a therapeutically effective amount of a therapeutic gene product (e.g., IL-1Ra). The methods and compositions may feature a recombinant self-complementary adeno-associated virus (sc-rAAV), wherein the sc-rAAV comprises an engineered capsid and a vector (e.g., a sc-rAAV vector) packaged within the capsid. The vector may comprise a transgene (e.g., a nucleotide sequence encoding a protein of interest, e.g., a therapeutic gene product, e.g., IL-1Ra or a codon modified version thereof) operably linked to a promoter (e.g., a constitutive promoter). The therapeutic gene product may be delivered to a location of interest, e.g., a joint. For example, for treating osteoarthritis, the sc-rAAV may be introduced into cells (e.g., chondrocytes, synoviocytes, etc.) in a joint via direct intraarticular injection. The present invention is not limited to the aforementioned conditions, nor the location of interest (e.g., joint).

It is noted that Goodrich et al. (Molecular Therapy-Nucleic Acids, 2013, 2:e70) generally discloses a method of treating osteoarthritis using scAAV-delivered IL-1Ra. However, Goodrich et al. does not specifically identify or enable any particular IL-1Ra sequence, e.g., an IL-1Ra sequence according to the present invention. In particular, the field of gene therapy is an unpredictable area wherein one cannot assume that any particular gene sequence for a protein of interest will be efficiently expressed. Moreover, gene therapy is also unpredictable with respect to effectiveness in animal model compared to humans, e.g., one cannot assume that if a particular method is effective in an animal model that it will be effective in humans.

SUMMARY OF THE INVENTION

The present invention features a recombinant self-complementary adeno-associated virus (sc-rAAV). In some embodiments, the sc-rAAV comprises an engineered AAV capsid and a vector packaged within the capsid, wherein the vector comprises a modified IL-1Ra gene operably linked to a promoter and the modified IL-1Ra gene is at least 95% identical to SEQ ID NO: 2. In some embodiments, the promoter comprises a CMV promoter. In some embodiments, the engineered capsid comprises at least a portion of serotype AAV2 and at least a portion of serotype AAV6. In some embodiments, the engineered capsid comprises at least a portion of serotype AAV1, AAV2, AAV3, AAV4, AAV5, AAV6, AAV7, AAV8, AAV9, AAV10, AAV11, or a combination thereof. In some embodiments, the vector further comprises SV40 and bovine growth hormone (bGH) polyadenylation sequences. In some embodiments, the vector further comprises SV40 splice donor (SD) and splice acceptor (SA) sites. In some embodiments, the vector comprises sc-rAAV2.5Hu-IL-1Ra. In some embodiments, the sc-rAAV is part of a composition.

In some embodiments, the sc-rAAV comprises an engineered AAV capsid and a vector packaged within the capsid, wherein the vector comprises a modified IL-1Ra gene operably linked to a promoter and the modified IL-1Ra gene encodes IL-1Ra protein according to SEQ ID NO: 6.

The present invention features a method of providing a human in need thereof (e.g., a human diagnosed with or at risk for osteoarthritis or rheumatoid arthritis) a therapeutically effective amount of interleukin-1 receptor agonist (IL-1Ra) peptide. In some embodiments, the method comprises introducing into a location of interest (e.g., via intraarticular injection) a composition comprising a recombinant self-complementary adeno-associated virus (sc-rAAV) according to the present invention. The sc-rAAV transduces the vector into cells in the location of interest, wherein the modified IL-1Ra gene is expressed so as to provide the human with the therapeutically effective amount of said IL-1Ra peptide.

The present invention also features a method of ameliorating symptoms of osteoarthritis or rheumatoid arthritis in a human. In some embodiments, the method comprises introducing into a location of interest (e.g., via direct intraarticular injection) a composition comprising a recombinant self-complementary adeno-associated virus (sc-rAAV) according to the present invention. The sc-rAAV transduces the vector into cells in the location of interest, wherein the modified IL-1Ra gene is expressed so as to provide the human with an amount of IL-1Ra peptide effective for ameliorating symptoms associated with osteoarthritis or rheumatoid arthritis.

The present invention also features a method of repairing cartilage in a human in need thereof (e.g., a human diagnosed with or at risk for developing osteoarthritis or rheumatoid arthritis). In some embodiments, the method comprises introducing into a location of cartilage (e.g., via direct intraarticular injection) a composition comprising a recombinant self-complementary adeno-associated virus (sc-rAAV) according to the present invention. The sc-rAAV transduces the vector into cells in the location of cartilage, wherein the modified IL-1Ra gene is expressed so as to provide the human with IL-1Ra peptide effective for repairing cartilage.

The present invention also features a method of providing interleukin-1 receptor agonist (IL-1Ra) peptide to an area of inflammation. In some embodiments, the method comprises introducing into a location of inflammation (e.g., via intraarticular injection) a composition comprising a recombinant self-complementary adeno-associated virus (sc-rAAV) according to the present invention. The sc-rAAV transduces the vector into cells in the location of inflammation, wherein the modified IL-1Ra gene is expressed so as to provide the cells in the location of inflammation a therapeutically effective amount of IL-1Ra peptide effective for reducing inflammation.

In some embodiments, the location of interest is a joint, synovium, subsynovium, joint capsule, tendon, ligament, cartilage, or peri-articular muscle of the human. In some embodiments, the cells are chondrocytes, synoviocytes, or a combination thereof.

In some embodiments, the method is performed a second time at a time point after a time when the method is performed first. In some embodiments, the time point is at least 3 months. In some embodiments, the method further comprises co-introducing a secondary therapy (e.g., a glucocorticoid, hyaluronan, platelet-rich plasma, recombinant, human IL-1Ra, or a combination thereof) to the location of interest in combination with the composition.

The present invention also features a method of delivering IL-1Ra peptide to a chondrocyte or synoviocyte. In some embodiments, the method comprises contacting the chondrocyte or synoviocyte with a recombinant self-complementary adeno-associated virus (sc-rAAV) according to the present invention, e.g., an engineered adeno-associated virus (AAV) capsid comprising at least a portion of serotype 2 and at least a portion of serotype 6 and a vector packaged within the capsid, wherein the vector comprises a modified IL-1Ra gene operably linked to a CMV promoter and the modified IL-1Ra gene is at least 95% identical to SEQ ID NO: 2. The sc-rAAV transduces the vector into the chondrocyte or synoviocyte and the modified IL-1Ra gene is expressed to as to provide IL-1Ra peptide to the chondrocyte or synoviocyte.

For the aforementioned methods and compositions (e.g., a method of providing a human in need thereof a therapeutically effective amount of interleukin-1 receptor agonist (IL-1Ra) peptide, a method of ameliorating symptoms of osteoarthritis or rheumatoid arthritis in a human, a method of delivering IL-1Ra peptide to a chondrocyte or synoviocyte, a composition comprising a recombinant self-complementary adeno-associated virus (sc-rAAV), a recombinant self-complementary adeno-associated virus (sc-rAAV) vector comprising a modified IL-1Ra gene operably linked to a CMV promoter, a method of repairing cartilage in a canine in need thereof, a method of providing interleukin-1 receptor agonist (IL-1Ra) peptide to an area of inflammation, etc.), the modified IL-1Ra gene may be at least 95% identical SEQ ID NO: 2 and encode IL-1Ra according to SEQ ID NO: 6.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

FIG. 1 shows Plasmid sc-rAAV2.5Hu-IL-1Ra, which contains a modified cDNA encoding the human IL-1Ra protein under control of the CMV promoter. The gene insert also contains SV40 and bovine growth hormone (bGH) polyadenylation sequences, as well as SV40 splice donor (SD) and splice acceptor (SA) sites. The region between inverted terminal repeats (TR) has been verified by sequencing.

TERMS

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including A and B."

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999, the disclosures of which are incorporated in their entirety herein by reference.

All publications, patent applications, patents, and other references mentioned herein are incorporated by reference in their entirety.

Although methods and materials similar or equivalent to those described herein can be used to practice or test the disclosed technology, suitable methods and materials are described below. The materials, methods, and examples are illustrative only and not intended to be limiting.

In order to facilitate review of the various embodiments of the disclosure, the following explanations of specific terms are provided:

Adeno-associated virus (AAV), Recombinant AAV (rAAV), and Recombinant Self-Complementary AAV (sc-rAAV): AAV is a small virus (20 nm) in the family Parvoviridae. AAV is not known to cause disease. AAV has recently been used to gene therapy for a variety of reasons including that it has been shown to have low immunogenicity, the ability to effectively transduce non-dividing cells, and the ability to infect a variety of cell and tissue types. Recombinant AAV (rAAV) does not contain native viral coding sequences. Recombinant AAV DNA is packaged into the viral capsid as a single stranded molecule about 4600 nucleotides in length. Following infection of the cell by the virus, the molecular machinery of the cell converts the single DNA strand into a double-stranded form. Only the double stranded DNA form is useful to the proteins of the cell that transcribe the contained gene or genes into RNA. Self-complementary AAV (sc-rAAV) is an engineered form of rAAV that can form an intra-molecular double stranded DNA template. Thus, upon infection, the two complementary halves of sc-rAAV will associate to form one double stranded DNA unit that is ready for immediate replication and synthesis.

Expression: The translation of a nucleic acid sequence into a protein. Proteins may be expressed and remain intracellular, become a component of the cell surface membrane, or be secreted into the extracellular matrix or medium.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence.

Pharmaceutically acceptable vehicles: Pharmaceutically acceptable carriers (vehicles), e.g., solutions, may be conventional but are not limited to conventional vehicles. For example, E. W. Martin, *Remington's Pharmaceutical Sciences*, Mack Publishing Co., Easton, Pa., 15th Edition (1975) and D. B. Troy, ed. Remington: The Science and Practice of Pharmacy, Lippincott Williams & Wilkins, Baltimore Md. and Philadelphia, Pa., 21$^{st}$ Edition (2006) describe compositions and formulations suitable for pharmaceutical delivery of one or more therapeutic compounds or molecules. In general, the nature of the carrier will depend on the particular mode of administration being employed. In addition to biologically-neutral carriers, pharmaceutical compositions administered may contain minor amounts of non-toxic auxiliary substances, such as wetting or emulsifying agents, preservatives, and pH buffering agents and the like, for example sodium acetate or sorbitan monolaurate.

Preventing, treating, managing, or ameliorating a condition: "Preventing" a disease may refer to inhibiting the full development of a condition. "Treating" may refer to a therapeutic intervention that ameliorates a sign or symptom of a disease or pathological condition after it has begun to develop. "Managing" may refer to a therapeutic intervention that does not allow the signs or symptoms of a disease or condition to worsen. "Ameliorating" may refer to the reduction in the number or severity of signs or symptoms of a disease or condition.

Sequence identity: The identity (or similarity) between two or more nucleic acid sequences is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. ScL USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., Meth. Mol. Bio. 24:307-31, 1994. Altschul et al., *J. Mol. Biol.* 215:403-10, 1990, presents a detailed consideration of sequence alignment methods and homology calculations. The NCBI Basic Local Alignment Search Tool (BLAST) (Altschul et al., *J. Mol. Biol.* 215:403-10, 1990) is available from several sources, including the National Center for Biotechnology (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site. BLASTN may be used to compare nucleic acid sequences, while BLASTP may be used to compare amino acid sequences. If the two compared sequences share homology, then the designated output file will present those regions of homology as aligned sequences. If the two compared sequences do not share homology, then the designated output file will not present aligned sequences. The BLAST-like alignment tool (BLAT) may also be used to compare nucleic acid sequences (Kent, Genome Res. 12:656-664, 2002). BLAT is available from several sources, including Kent Informatics (Santa Cruz, Calif.) and on the Internet (genome.ucsc.edu). Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth.

Therapeutically effective amount: A quantity of a specified agent sufficient to achieve a desired effect in a subject being treated with that agent. Such agents may include IL-1Ra. For example, a therapeutically effective amount of IL-1Ra may be an amount sufficient to prevent, treat, or ameliorate symptoms of osteoarthritis or rheumatoid arthritis. The therapeutically effective amount of an agent useful for preventing, ameliorating, and/or treating a subject will be dependent on the subject being treated, the type and severity of the affliction, and the manner of administration of the therapeutic composition.

Transduced: A transduced cell is a cell into which a nucleic acid molecule has been introduced by molecular biology techniques. As used herein, the term transduction encompasses all techniques by which a nucleic acid molecule might be introduced into such a cell, including transfection with viruses or viral vectors, transformation with plasmid vectors, and introduction of naked DNA by electroporation, lipofection, and particle gun acceleration. Such cells are sometimes called transformed cells.

Vector: A nucleic acid molecule as introduced into a host cell, thereby producing a transformed host cell. A vector may include nucleic acid sequences that permit it to replicate in a host cell, such as an origin of replication. A vector may lack the nucleic acid sequences that permit it to replicate in a host cell. A vector may also include a gene of interest, one or more selectable marker genes, other genetic elements known in the art, or any other appropriate insert.

DETAILED DESCRIPTION OF THE INVENTION

The present invention features methods and compositions for delivering a therapeutic gene product (e.g., IL-1Ra) in a sustained manner to a location of interest, e.g., a joint. The present invention also features methods and compositions for treating symptoms of conditions such as but not limited to osteoarthritis or rheumatoid arthritis. The present invention also features methods and compositions for providing an individual (e.g., a human) a therapeutically effective amount of a therapeutic gene product (e.g., IL-1Ra). The methods and compositions may feature a recombinant self-complementary adeno-associated virus (sc-rAAV), wherein the sc-rAAV comprises an engineered capsid and a vector (an sc-rAAV vector) packaged within the capsid. The vector may comprise a transgene (e.g., a nucleotide sequence encoding a protein of interest, e.g., a therapeutic gene product, e.g., IL-1Ra or a modified version thereof) operably linked to a promoter (e.g., a constitutive promoter).

As previously discussed, the present invention features compositions comprising a recombinant self-complementary adeno-associated virus (sc-rAAVs) vector. A non-limiting example of a sc-rAAV vector is shown in SEQ ID NO: 1 of Table 1 below. The sc-rAAV vector of SEQ ID NO: 1 comprises a modified IL-1Ra gene. In some embodiments, the vector comprises SV40 polyadenylation sequences. In some embodiments, the vector comprises bovine growth hormone (bGH) polyadenylation sequences. In some embodiments, the vector comprises SV40 splice donor (SD) and splice acceptor (SA) sites. The sc-rAAV vector is not limited to SEQ ID NO: 1.

The sc-rAAV vectors comprise a nucleic acid that encodes a peptide of interest. In some embodiments, the nucleic acid is at least 90% identical to SEQ ID NO: 2. In some embodiments, the nucleic acid is at least 92% identical to SEQ ID NO: 2. In some embodiments, the nucleic acid is at least 94% identical to SEQ ID NO: 2. In some embodiments, the nucleic acid is at least 95% identical to SEQ ID NO: 2. In some embodiments, the nucleic acid is at least 96% identical to SEQ ID NO: 2. In some embodiments, the nucleic acid is at least 97% identical to SEQ ID NO: 2. In some embodiments, the nucleic acid is at least 98% identical to SEQ ID NO: 2. In some embodiments, the nucleic acid is at least 99% identical to SEQ ID NO: 2. Non-limiting examples of such nucleic acid sequences can be found in Table 1 below. For example, SEQ ID NO: 3 is a sequence for a modified human IL-1Ra that is about 98% identical to SEQ ID NO: 2; SEQ ID NO: 4 is a sequence for a modified human IL-1Ra that is about 99% identical to SEQ ID NO: 2; and (note that the bold letters in Table 1 are nucleotide substitutions as compared to SEQ ID NO: 2, and the codon underlined).

TABLE 1

| SEQ ID NO: | DESCRIPTION | SEQUENCE |
|---|---|---|
| 1 | Sequence of Hu-IL-1Ra plasmid containing entire viral sequence with modified human IL1Ra insert (underlined) and the SacII/NotI restriction sites in bold italics. | CATTAATGAATCGGCCAACGCGCGGGGAGAGGCGGTTTGCGTATTGGG CGCTCTTCCGCTTCCTCGCTCACTGACTCGCTGCGCTCGGTCGTTCGG CTGCGGCGAGCGGTATCAGCTCACTCAAAGGCGGTAATACGGTTATCC ACAGAATCAGGGGATAACGCAGGAAAGAACATGTGAGCAAAAGGCCAG CAAAAGGCCAGGAACCGTAAAAAGGCCGCGTTGCTGGCGTTTTTCCAT AGGCTCCGCCCCCCTGACGAGCATCACAAAAATCGACGCTCAAGTCAG AGGTGGCGAAACCCGACAGGACTATAAAGATACCAGGCGTTTCCCCCT GGAAGCTCCCTCGTGCGCTCTCCTGTTCCGACCCTGCCGCTTACCGGA TACCTGTCCGCCTTTCTCCCTTCGGGAAGCGTGGCGCTTTCTCATAGC TCACGCTGTAGGTATCTCAGTTCGGTGTAGGTCGTTCGCTCCAAGCTG GGCTGTGTGCACGAACCCCCCGTTCAGCCCGACCGCTGCGCCTTATCC GGTAACTATCGTCTTGAGTCCAACCCGGTAAGACACGACTTATCGCCA CTGGCAGCAGCCACTGGTAACAGGATTAGCAGAGCGAGGTATGTAGGC GGTGCTACAGAGTTCTTGAAGTGGTGGCCTAACTACGGCTACACTAGA AGGACAGTATTTGGTATCTGCGCTCTGCTGAAGCCAGTTACCTTCGGA AAAAGAGTTGGTAGCTCTTGATCCGGCAAACAAACCACCGCTGGTAGC GGTGGTTTTTTTGTTTGCAAGCAGCAGATTACGCGCAGAAAAAAAGGA TCTCAAGAAGATCCTTTGATCTTTTCTACGGGGTCTGACGCTCAGTGG AACGAAAACTCACGTTAAGGGATTTTGGTCATGAGATTATCAAAAAGG ATCTTCACCTAGATCCTTTTAAATTAAAAATGAAGTTTTAAATCAATC TAAAGTATATATGAGTAAACTTGGTCTGACAGTTACCAATGCTTAATC AGTGAGGCACCTATCTCAGCGATCTGTCTATTTCGTTCATCCATAGTT GCCTGACTCCCCGTCGTGTAGATAACTACGATACGGGAGGGCTTACCA TCTGGCCCCAGTGCTGCAATGATACCGCGAGACCCACGCTCACCGGCT CCAGATTTATCAGCAATAAACCAGCCAGCCGGAAGGGCCGAGCGCAGA |

TABLE 1-continued

| SEQ ID NO: DESCRIPTION | SEQUENCE |
|---|---|
| | AGTGGTCCTGCAACTTTATCCGCCTCCATCCAGTCTATTAATTGTTGC
CGGGAAGCTAGAGTAAGTAGTTCGCCAGTTAATAGTTTGCGCAACGTT
GTTGCCATTGCTACAGGCATCGTGGTGTCACGCTCGTCGTTTGGTATG
GCTTCATTCAGCTCCGGTTCCCAACGATCAAGGCGAGTTACATGATCC
CCCATGTTGTGCAAAAAAGCGGTTAGCTCCTTCGGTCCTCCGATCGTT
GTCAGAAGTAAGTTGGCCGCAGTGTTATCACTCATGGTTATGGCAGCA
CTGCATAATTCTCTTACTGTCATGCCATCCGTAAGATGCTTTTCTGTG
ACTGGTGAGTACTCAACCAAGTCATTCTGAGAATAGTGTATGCGGCGA
CCGAGTTGCTCTTGCCCGGCGTCAATACGGGATAATACCGCGCCACAT
AGCAGAACTTTAAAAGTGCTCATCATTGGAAAACGTTCTTCGGGGCGA
AAACTCTCAAGGATCTTACCGCTGTTGAGATCCAGTTCGATGTAACCC
ACTCGTGCACCCAACTGATCTTCAGCATCTTTTACTTTCACCAGCGTT
TCTGGGTGAGCAAAAACAGGAAGGCAAAATGCCGCAAAAAAGGGAATA
AGGGCGACACGGAAATGTTGAATACTCATACTCTTCCTTTTTCAATAT
TATTGAAGCATTTATCAGGGTTATTGTCTCATGAGCGGATACATATTT
GAATGTATTTAGAAAAATAAACAAATAGGGGTTCCGCGCACATTTCCC
CGAAAAGTGCCACCTGACGTCTAAGAAACCATTATTATCATGACATTA
ACCTATAAAAATAGGCGTATCACGAGGCCCTTTCGTCTCGCGCGTTTC
GGTGATGACGGTGAAAACCTCTGACACATGCAGCTCCCGGAGACGGTC
ACAGCTTGTCTGTAAGCGGATGCCGGGAGCAGACAAGCCCGTCAGGGC
GCGTCAGCGGGTGTTGGCGGGTGTCGGGGCTGGCTTAACTATGCGGCA
TCAGAGCAGATTGTACTGAGAGTGCACCATATGCGGTGTGAAATACCG
CACAGATGCGTAAGGAGAAAATACCGCATCAGGAATTCCAACATCCAA
TAAATCATACAGGCAAGGCAAAGAATTAGCAAAATTAAGCAATAAAGC
CTCAGAGCATAAAGCTAAATCGGTTGTACCAAAAACATTATGACCCTG
TAATACTTTTGCGGGAGAAGCCTTTATTTCAACGCAAGGATAAAAATT
TTTAGAACCCTCATATATTTTAAATGCAATGCCTGAGTAATGTGTAGG
TAAAGATTCAAACGGGTGAGAAAGGCCGGAGACAGTCAAATCACCATC
AATATGATATTCAACCGTTCTAGCTGATAAATTCATGCCGGAGAGGT
AGCTATTTTTGAGAGGTCTCTACAAAGGCTATCAGGTCATTGCCTGAG
AGTCTGGAGCAAACAAGAGAATCGATGAACGGTAATCGTAAAACTAGC
ATGTCAATCATATGTACCCCGGTTGATAATCAGAAAAGCCCCAAAAAC
AGGAAGATTGTATAAGCAAATATTTAAATTGTAAACGTTAATATTTTG
TTAAAATTCGCGTTAAATTTTTGTTAAATCAGCTCATTTTTTAACCAA
TAGGCCGAAATCGGCAAAATCCCTTATAAATCAAAAGAATAGACCGAG
ATAGGGTTGAGTGTTGTTCCAGTTTGGAACAAGAGTCCACTATTAAAG
AACGTGGACTCCAACGTCAAAGGGCGAAAAACCGTCTATCAGGGCGAT
GGCCCACTACGTGAACCATCACCCTAATCAAGTTTTTTGGGGTCGAGG
TGCCGTAAAGCACTAAATCGGAACCCTAAAGGGAGCCCCCGATTTAGA
GCTTGACGGGGAAAGCCGGCGAACGTGGCGAGAAAGGAAGGGAAGAAA
GCGAAAGGAGCGGGCGCTAGGGCGCTGGCAAGTGTAGCGGTCACGCTG
CGCGTAACCACCACACCCGCCGCGCTTAATGCGCCGCTACAGGGCGCG
TACTATGGTTGCTTTGACGAGCACGTATAACGTGCTTTCCTCGTTAGA
ATCAGAGCGGGAGCTAAACAGGAGGCCGATTAAAGGGATTTTAGACAG
GAACGGTACGCCAGAATCCTGAGAAGTGTTTTTATAATCAGTGAGGCC
ACCGAGTAAAAGAGTCTGTCCATCACGCAAATTAACCGTTGTCGCAAT
ACTTCTTTGATTAGTAATAACATCACTTGCCTGAGTAGAAGAACTCAA
ACTATCGGCCTTGCTGGTAATATCCAGAACAATATTACCGCCAGCCAT
TGCAACAGGAAAACGCTCATGGAAATACCTACATTTTGACGCTCAAT
CGTCTGGAATTCCATTCGCCATTCAGGCTGCGCAACTGTTGGGAAGGG
CGATCGGTGCGGGCCTCTTCGCTATTACGCCAGCTGGCGCGCTCGCTC
GCTCACTGAGGCCGCCCGGGCAAAGCCCGGGCGTCGGGCGACCTTTGG
TCGCCCGGCCTCAGTGAGCGAGCGAGCGCGCAGAGAGGGAGTGGCCAA
CTCCATCACTAGGGGTTCCTTGTAGTTAATGATTAACCCGCCATGCTA
CTTATCTACGTAGCCATGCTCGATCTGAATTCGGTACCCGTTACATAA
CTTACGGTAAATGGCCCGCCTGGCTGACCGCCCAACGACCCCCGCCCA
TTGACGTCAATAATGACGTATGTTCCCATAGTAACGCCAATAGGGACT
TTCCATTGACGTCAATGGGTGGAGTATTTACGGTAAACTGCCCACTTG
GCAGTACATCAAGTGTATCATATGCCAAGTACGCCCCCTATTGACGTC
AATGACGGTAAATGGCCCGCCTGGCATTATGCCCAGTACATGACCTTA
TGGGACTTTCCTACTTGGCAGTACATCTACGTATTAGTCATCGCTATT
ACCATGGTGATGCGGTTTTGGCAGTACATCAATGGGCGTGGATAGCGG
TTTGACTCACGGGGATTTCCAAGTCTCCACCCCATTGACGTCAATGGG
AGTTTGTTTTGGCACCAAAATCAACGGGACTTTCCAAAATGTCGTAAC
AACTCCGCCCCATTGACGCAAATGGGCGGTAGGCGTGTACGGTGGGAG
GTCTATATAAGCAGAGCTCGTTTAGTGAACCGTCAGATCGCCTGGAGA
CGCCATCCACGCTGTTTTGACCTCCATAGAAGACACCGGGACCGATCC
AGCCTCCGGACTCTAGAGGATCCGGTACTCGAGGAACTGAAAAACCAG
AAAGTTAACTGGTAAGTTTAGTCTTTTTGTCTTTTATTTCAGGTCCCG
GATCCGGTGGTGGTGCAAATCAAAGAACTGCTCCTCAGTGGATGTTGC
CTTTACTTCTAGGCCTGTACGGAAGTGTTACTTCTGCTCTAAAAGCTG
CGGAATTGTAC *CCGCGGG*CCACC<u>ATGGAAATCTGCAGAGGCCTGCGG</u>
<u>AGCCACCTGATTACCCTGCTGCTGTTCCTGTTCCACAGCGAGACAATC</u>
<u>TGCCGGCCCAGCGGCCGGAAGTCCAGCAAGATGCAGGCCTTCCGGATC</u>
<u>TGGGACGTGAACCAGAAAACCTTCTACCTGCGGAACAACCAGCTGGTG</u>
<u>GCCGGATACCTGCAGGGCCCCAACGTGAACCTGGAAGAGAAGATCGAC</u> |

TABLE 1-continued

| SEQ ID NO: DESCRIPTION | SEQUENCE |
|---|---|
| | GTGGTGCCCATCGAGCCCCACGCCCTGTTTCTGGGCATCCACGGCGGC<br>AAGATGTGCCTGAGCTGCGTGAAGTCCGGCGACGAGACAAGACTGCAG<br>CTGGAAGCCGTGAACATCACCGACCTGAGCGAGAACCGGAAGCAGGAC<br>AAGAGATTCGCCTTCATCAGAAGCGACAGCGGCCCCACCACCAGCTTT<br>GAGAGCGCCGCCTGCCCCGGCTGGTTCCTGTGTACAGCCATGGAAGCC<br>GACCAGCCCGTGTCCCTGACAAACATGCCCGACGAGGGCGTGATGGTC<br>ACCAAGTTCTATTTTCAAGAAGATGAGTAATAA *GCGGCCGC*CGGGAT<br>CCAGACATGATAAGATACATTGATGAGTTTGGACAAACCACAACTAGA<br>ATGCAGTGAAAAAAATGCTTTATTTGTGAAATTTGTGATGCTATTGCT<br>TTATTTGTAACCATTATAAGCTGCAATAAACAAGTTAACAACAACAAT<br>TGCATTCATTTTATGTTTCAGGTTCAGGGGGAGGTGTGGGAGGTTTTT<br>TAGTCGACTAGAGCTCGCTGATCAGCCTCGACTGTGCCTTCTAGTTGC<br>CAGCCATCTGTTGTTTGCCCCTCCCCCGTGCCTTCCTTGACCCTGGAA<br>GGTGCCACTCCCACTGTCCTTTCCTAATAAAATGAGGAAATTGCATCG<br>CATTGTCTGAGTAGGTGTCATTCTATTCTGGGGGGTGGGGTGGGGCAG<br>GACAGCAAGGGGGAGGATTGGGAAGACAATAGCAGGAACCCCACTCCC<br>TCTCTGCGCGCTCGCTCGCTCACTGAGGCCGGGCGACCAAAGGTCGCC<br>CGACGCCCGGGCTTTGCCCGGGCGGCCTCAGTGAGCGAGCGAGCGCGC<br>AGCTGCTG |
| 2 Modified human IL-1Ra insert | ATGGAAATCTGCAGAGGCCTGCGGAGCCACCTGATTACCCTGCTGCTG<br>TTCCTGTTCCACAGCGAGACAATCTGCCGGCCCAGCGGCCGGAAGTCC<br>AGCAAGATGCAGGCCTTCCGGATCTGGGACGTGAACCAGAAAACCTTC<br>TACCTGCGGAACAACCAGCTGGTGGCCGGATACCTGCAGGGCCCCAAC<br>GTGAACCTGGAAGAGAAGATCGACGTGGTGCCCATCGAGCCCCACGCC<br>CTGTTTCTGGGCATCCACGGCGGCAAGATGTGCCTGAGCTGCGTGAAG<br>TCCGGCGACGAGACAAGACTGCAGCTGGAAGCCGTGAACATCACCGAC<br>CTGAGCGAGAACCGGAAGCAGGACAAGAGATTCGCCTTCATCAGAAGC<br>GACAGCGGCCCCACCACCAGCTTTGAGAGCGCCGCCTGCCCCGGCTGG<br>TTCCTGTGTACAGCCATGGAAGCCGACCAGCCCGTGTCCCTGACAAAC<br>ATGCCCGACGAGGGCGTGATGGTCACCAAGTTCTATTTTCAAGAAGAT<br>GAGTAATAA |
| 3 Modified human IL-1Ra insert (98% identical to SEQ ID NO: 2; bold letters are nucleotide substitutions within a codon (codon is underlined)) | ATGGAAATCTGCAGA<u>GGA</u>CTGCGGAGCCAC<u>CTA</u>ATTACC<u>CTA</u>CT<u>CCT</u>T<br>TTCCTGTTCCACAGCGAGACAATCTGCCGGCCCAGCGGCCGGAAGTCC<br>AGCAAGATGCAG<u>GCT</u>TTCCGGATCTGGGACGTGAACCAGAAAACCTTC<br>TAC<u>CTC</u>CGGAACAACCAGCTGGTG<u>GCG</u>GGATACC<u>TCC</u>AGGGCCCCAAC<br>GTGAAC<u>CTA</u>GAAGAGAAGATCGACGTGGTGCCCATCGAGCCCCACGCC<br>CTGTTTCTGGGCATCCACGGCGGCAAGATGTGCCTGAGCTGCGTGAAG<br>TCCGGCGACGAGACAAGACTGCAGCTGGAAGCCGTGAACATCACCGAC<br>CTGAGCGAGAACCGGAAGCAGGACAAGAGATTCGCCTTCATCAGAAGC<br>GACAGCGGCCCCACCACCAGCTTTGAGAGCGCCGCCTGCCCCGGCTGG<br>TTCCTGTGTACAGCCATGGAAGCCGACCAGCCCGTGTCCCTGACAAAC<br>ATGCCCGACGAGGGCGTGATGGTCACCAAGTTCTATTTTCAAGAAGAT<br>GAGTAATAA |
| 4 Modified human IL-1Ra insert (99% identical to SEQ ID NO: 2; bold letters are nucleotide substitutions within a codon (codon is underlined)) | ATGG<u>AG</u>ATCTGCAGAGGCCTGCGGAGC<u>CAT</u>CTGATTACC<u>CTA</u>CTG<u>CTT</u><br>TTCCTGTTC<u>CAT</u>AGCGAGACAATCTGCCGGCCCAGCGGCCGGAAGTCC<br>AGC<u>AAA</u>ATGCAGGCCTTCCGGATCTGGGACGTGAACCAGAAAACCTTC<br>TACCTGCGGAACAACCAGCTGGTGGCCGGATACCTGCAGGGCCCCAAC<br>GTGAACCTGGAAGAGAAGATCGACGTGGTGCCCATCGAGCCCCACGCC<br>CTGTTTCTGGGCATCCACGGCGGCAAGATGTGCCTGAGCTGCGTGAAG<br>TCCGGCGACGAGACAAGACTGCAGCTGGAAGCCGTGAACATCACCGAC<br>CTGAGCGAGAACCGGAAGCAGGACAAGAGATTCGCCTTCATCAGAAGC<br>GACAGCGGCCCCACCACCAGCTTTGAGAGCGCCGCCTGCCCCGGCTGG<br>TTCCTGTGTACAGCCATGGAAGCCGACCAGCCCGTGTCCCTGACAAAC<br>ATGCCCGACGAGGGCGTGATGGTCACCAAGTTCTATTTTCAAGAAGAT<br>GAGTAATAA |
| 5 Modified human IL-1Ra insert (95% identical to SEQ ID NO: 2; bold letters are nucleotide substitutions within a codon (codon is underlined)) | ATGG<u>AG</u>ATCTGCAGA<u>GGA</u>CTGCGGAGCCAC<u>CTA</u>ATTACC<u>CTA</u>CT<u>CCT</u>T<br>TTCCTGTTC<u>CAT</u>AGCGAGACAATCTGCCGGCCCAGCGGCCGGAAGTCC<br>AGC<u>AAA</u>ATGCAG<u>GCT</u>TTCCGGATCTGG<u>GAT</u>GTGAACCAG<u>AAG</u>ACCTTC<br>TAC<u>CTC</u>CGGAACAACCAGCTGGTG<u>GCG</u>GGATACC<u>TCC</u>AGGGCCCCAAC<br>GTGAAC<u>CTA</u>GAAGAGAAGATCGACGTGGTGCCCATCGAGCCCCACGCC<br>CTGTTTCTGGGCATC<u>CAT</u>GGCGGCAAGATG<u>TGT</u>CT<u>GAGT</u>TGCGTGAAG<br><u>TCA</u>GGCGACGAGACAAGACTGCAGCTGGAAGCCGTGAACATCACCGAC<br>CTGAGC<u>GAA</u>AACCGGAAGCAGGACAAGAGATTCGCCTTCATCAGAAGC<br>GACAGCGGCCCCACC<u>ACT</u>AGCTTTGAGAGC<u>GCA</u>GCCTGCCCCGGCTGG<br>TTCCTGTGTACAGCCATG<u>GAG</u>GCCGACCAGCCCGTGTCCCTGACAAAC<br>ATG<u>CCT</u>GAC<u>GAA</u>GGCGTGATGGTCACCAAGTTC<u>TAC</u>TTTCAAGAAGAT<br>G<u>AA</u>TAATAA |

In some embodiments, the IL-1Ra peptide encoded by the IL-1Ra insert comprises IL-1Ra (see SEQ ID NO: 6 in Table 2 below).

TABLE 2

| SEQ ID NO: | DESCRIPTION | SEQUENCE |
|---|---|---|
| 6 | IL-1Ra (UNIPROT P18510) | MEICRGLRSH LITLLLFLFH SETICRPSGR KSSKMQAFRI WDVNQKTFYL RNNQLVAGYL QGPNVNLEEK IDVVPIEPHA LFLGIHGGKM CLSCVKSGDE TRLQLEAVNI TDLSENRKQD KRFAFIRSDS GPTTSFESAA CPGWFLCTAM EADQPVSLTN MPDEGVMVTK FYFQEDE |

The transgene (e.g., nucleotide sequence encoding protein of interest) is operably linked to a promoter. In some embodiments, the promoter comprises the cytomegalovirus (CMV) promoter. The present invention is not limited to the CMV promoter and may feature any appropriate promoter or portions of various promoters. Examples of promoters include CMV promoter, hybrid CMV promoter, CAG promoter, human beta-actin promoter, hybrid beta-actin promoter, EF1 promoter, U1a promoter, U1b promoter, a Tet-inducible promoter, a VP16-LexA promoter, chicken beta-actin (CBA) promoter, human elongation factor-1alpha promoter, simian virus 40 (SV40) promoter, and herpes simplex virus thymidine kinase promoter.

In some embodiments, the promoter comprises a hybrid promoter. As an example, Table 3 shows an IL-1 beta/IL-6 hybrid promoter (see also van de Loo et al., 2004, Gene Therapy 11:581-590). The present invention is also not limited to the hybrid promoter shown in Table 3.

TABLE 3

| SEQ ID NO: | DESCRIPTION | SEQUENCE |
|---|---|---|
| 7 | IL-1 beta/ IL-6 hybrid promoter | atccaagag ggagaagaag cccattggag atgatgccat aaaggaagtg gaagcgatat gataaaaatc atagtgccca ttcccaaata atcccagaag cagaagggaa aggagagaaa tatccacaaa gacaggtgtg ggtacacaca acattttca tactttaaga tcccagagga ctcatggaaa tgatacaaga aaatgactca taagaacaaa tattaggaag ccagtgccaa gaatgagatg ggaaattggg gaaaatgttg ggggcagatt gcttagttct gttctaagca agagggtgaa caaggaagga acagctcact acaaagaaca gacatcactg catgtacaca caataatata agaactaacc catgattatt ttgcttgtct tcttgttcaa aatgattgaa gaccaatgag atgagatcaa ccttgataac tggctggctt cggcatgatt agacacaaga tggtatcagg gcacttgctg ctttgaataa tgtcagtctc ctgtcttgga agaatgacct gacagggtaa agaggaactt gcagctgaga aaggctttag tgactcaaga gctgaataat tccccaaaag ctggagcatc ctggcatttc cagctcccca tctctgcttg ttccacttcc ttggggctac atcaccatct acatcatcat cactcttcca ctccctccct tagtgccaac tatgtttata gcgagatatt ttctgctcat tggggatcgg aaggaagtgc tgtggcctga gcggtctcct tgggaagaca ggatctgata catacgttgc acaacctatt tgacataaga ggtttcactt cctgagatgg atgggatggt agcagatttg ggtccaggtt acagggccag gatgagacat ggcagaactg tggagactgt tacgtcaggg ggcattgccc catggctcca aaatttccct cgagc ctctggccc |

TABLE 3-continued

| SEQ ID NO: | DESCRIPTION | SEQUENCE |
|---|---|---|
| | | cacccctcacc ctccaacaaa gatttatcaa atgtgggatt ttcccatgag tctcaatatt agagtctcaa cccccaataa atataggact ggagatgtct gaggctcatt ctgccctcga gcccaccggg aacgaaagag aagctctatc tcccctccag gagcccagct atgaactcct tc |

In some embodiments, the sc-rAAV vector is packaged within a capsid. In some embodiments, the capsid comprises at least a portion of AAV serotype 1 (AAV1), AAV serotype 2, (AAV2), AAV serotype 3, (AAV3), AAV serotype 4, (AAV4), AAV serotype 5, (AAV5), AAV serotype 6, (AAV6), derivatives thereof, or combination thereof. For example, in some embodiments, the capsid comprises at least a portion of AAV serotype 2 and at least a portion of AAV serotype 6, e.g., AAV2.5.

The composition, e.g., the composition comprising the sc-rAAV, may be introduced into cells in a location of interest (e.g., in a human). For example, in some embodiments when treating symptoms of osteoarthritis, the composition may be introduced into cells (e.g., chondrocytes, synoviocytes, e.g., type A, type B, etc.) in a joint via direct intraarticular injection. In some embodiments, the composition is administered to a joint, synovium, subsynovium, joint capsule, tendon, ligament, cartilage, or peri-articular muscle of the human. The present invention is not limited to the aforementioned conditions (e.g., osteoarthritis), the means of administration (e.g., intraarticular injection), the location of interest (e.g., joint), or cell type (e.g., chondrocytes, synoviocytes). For example, in some embodiments, other cell types that may be transduced may include mesenchymal stem cells.

The sc-rAAV transduces the vector into cells and the modified IL-1Ra peptide is expressed. In some embodiments, the IL-1Ra peptide is expressed so as to provide the human with a therapeutically effective amount of said modified IL-1Ra peptide effective for ameliorating symptoms associated with various conditions such as osteoarthritis or rheumatoid arthritis.

In some embodiments, introduction of the composition (e.g., the sc-rAAV) is performed once. In some embodiments, introduction of the composition (e.g., the sc-rAAV) is performed twice, e.g., a first time and a second time subsequent to the first time. In some embodiments, introduction of the composition is performed more than two times, e.g., three times, four times, five times, etc. The introduction of the composition a second time may be performed at a time point after the time when the method is first performed, e.g., after 3 months, 4 months, 5 months, 6 months, 7 months, 8 months, 9 months, 10 months, 11 months, 1 year, more than one year, etc.

The composition may comprise any appropriate pharmaceutical composition. In some embodiments, the composition comprises a buffered solution. In some embodiments, the buffered solution comprises phosphate buffered saline (PBS). In some embodiments, the composition further comprises sorbitol, e.g., 5% sorbitol. In some embodiments, the composition further comprises a salt, e.g., NaCl. The concentration of salt may be any appropriate concentration, e.g., 350 mM NaCl, more than 350 mM NaCl, less then 350 mM, etc.

In some embodiments, the composition (e.g., the sc-rAAV) is co-administered with a secondary therapy. In some embodiments, the secondary therapy comprises a therapeutic for OA or RA or any other appropriate therapy for treating the symptoms of the condition. Non-limiting examples of secondary therapies for OA include glucocorticoids, hyaluronan (viscosupplementation), platelet-rich plasma, and recombinant, human IL-1Ra (Anakinra; Kineret®). For example, in some embodiments, the sc-rAAV is co-administered with glucocorticoids or platelet-rich plasma.

The disclosures of the following U.S. patents are incorporated in their entirety by reference herein: US2008/0187576, US2009/0104155, KR2012041139, JP2015518816, WO2013151672, WO2008088895, U.S. Pat. Nos. 8,529,885, 7,037,492, US20070128177, U.S. Pat. Nos. 6,491,907, 8,999,948, US20150218586, U.S. Pat. No. 7,892,824, US20130295614, JP2002538770, JP2010516252, KR2002027450, KR2003028080, U.S. Pat. No. 6,482,634, US20090105148, US20120232130, US20140234255, U.S. Pat. Nos. 5,756,283, 6,083,716, WO2002038782, WO2007039699, WO2012047093, WO2014170470, WO2015018860, WO2015044292, WO2015158749, U.S. Pat. Nos. 7,452,696, 6,943,153, 6,429,001, WO2015031392, WO2004092211.

Example 1

Example 1 describes administration of a sc-rAAV of the present invention (encoding IL-1Ra). The present invention is not limited to the disclosure of Example 1. Five patients enroll in a clinical trial investigating administration of a sc-rAAV of the present invention. The patients are as follows: (1) a 65 year old male with osteoarthritis in his right knee; (2) a 59 year old male with osteoarthritis in his left knee; (3) a 58 year old female with osteoarthritis in her left knee; (4) a 51 year old male with osteoarthritis in his right knee; and (5) a 48 year old male with osteoarthritis in his right knee. Each patient is administered the sc-rAAV via intraarticular injection at $1 \times 10^{12}$ viral genes per knee. IL-1Ra is expressed in the chondrocytes and synoviocytes. Patient 1 describes amelioration of OA-related symptoms within 2 weeks. Patient 2 describes amelioration of OA-related symptoms within 1 week. Patient 3 describes amelioration of OA-related symptoms within 5 weeks. Patient 4 describes amelioration of OA-related symptoms within 1 week. As of 6 weeks, Patient 5 describes no amelioration of OA-related symptoms.

Example 2

Example 2 describes a first administration of a sc-rAAV of the present invention (encoding IL-1Ra) and a second administration of the same sc-rAAV of the present invention after a period of time. The present invention is not limited to the disclosure of Example 2. A 55-year-old male presents with osteoarthritis in his right knee. His physician performs a single intra-articular injection of the sc-rAAV vector of the present invention (encoding IL-1Ra). The patient's symptoms are eliminated within 2 months. After 6 months, the physician administers a second (single) intra-articular injection of the same sc-rAAV vector (encoding IL-1Ra) of the present invention. The patient's symptoms are still absent 6 months following the second injection.

Example 3

Example 3 describes a first administration of a sc-rAAV of the present invention (encoding IL-1Ra) and a second administration of a sc-rAAV of the present invention (encoding IL-1Ra) different from the first sc-rAAV after a period of time. The present invention is not limited to the disclosure of Example 3. A 49-year-old female presents with osteoarthritis in her right ankle. Her physician performs a single intra-articular injection of the sc-rAAV vector of the present invention (encoding IL-1Ra). The patient's symptoms have improved within 5 months but are not eliminated. After 6 months, the physician administers a second (single) intra-articular injection of a different sc-rAAV vector (encoding IL-1Ra) of the present invention. Six months following the second injection, the patient's symptoms are eliminated.

Example 4

Example 4 describes co-administration of a sc-rAAV of the present invention (encoding IL-1Ra) and a secondary therapy. The present invention is not limited to the disclosure of Example 4. A 68-year-old male presents with osteoarthritis in his left knee. His physician performs a single intra-articular injection of both a sc-rAAV vector of the present invention (encoding IL-1Ra) and platelet-rich plasma. The patient's symptoms are eliminated within 2 months.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described embodiments of the present invention, it will be readily apparent to those skilled in the art that modifications may be made thereto which do not exceed the scope of the appended claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

Any reference numbers recited in the below claims are solely for ease of examination of this patent application, and are exemplary, and are not intended in any way to limit the scope of the claims to the particular features having the corresponding reference numbers in the drawings.

What is claimed is:

1. A nucleic acid vector comprising a nucleic acid molecule consisting of the nucleotide sequence as set forth in SEQ ID NO: 2 operably linked to a promoter, wherein the nucleic acid molecule encodes a biologically active interleukin-1 receptor agonist (IL-1Ra) protein.

2. The nucleic acid vector of claim 1, further comprising:
an SV40 and bovine growth hormone (bGH) polyadenylation sequence; and/or
SV40 splice donor (SD) and splice acceptor (SA) sites.

3. The nucleic acid vector of claim 1, wherein the promoter is selected from the group consisting of: a cytomegalovirus (CMV) promoter, GAG promoter, human beta-actin promoter, hybrid beta-actin promoter, EF1 promoter, U1a promoter, U1b promoter, a Tet-inducible promoter, a VP16-LexA promoter, chicken beta-actin (CBA) promoter, human elongation factor-1 alpha promoter, simian virus 40 (SV40) promoter, herpes simplex virus thymidine kinase promoter, and an IL-1 beta/IL-6 hybrid promoter.

4. A recombinant adeno-associated virus (rAAV) comprising the nucleic acid vector of claim 1 and a capsid, wherein the nucleic acid vector is packaged within the capsid.

5. The rAAV of claim 4, wherein the rAAV is a self-complementary rAAV.

6. The rAAV of claim 4, wherein the capsid comprises at least a portion of AAV1, AAV2, AAV3, AAV4, AAV5, AAV6, AAV7, AAV8, AAV9, AAV10, AAV11, or combinations thereof.

7. The rAAV of claim 6, wherein the capsid comprises at least a portion of serotype AAV2 and at least a portion of serotype AAV6.

* * * * *